United States Patent
Knappe et al.

(10) Patent No.: US 10,154,952 B2
(45) Date of Patent: *Dec. 18, 2018

(54) AGENT AND METHOD FOR THE TEMPORARY SHAPING OF KERATIN-CONTAINING FIBERS

(71) Applicant: Henkel AG & Co. KGaA, Duesseldorf (DE)

(72) Inventors: Thorsten Knappe, Schenefeld (DE); Pamela Kaftan, Hamburg (DE); Maria Catalina Bermudez Agudelo, Hamburg (DE); Tim Bethge, Hamburg (DE)

(73) Assignee: Henkel AG & Co. KGaA, Duesseldorf (DE)

(*) Notice: Subject to any disclaimer, the term of this patent is extended or adjusted under 35 U.S.C. 154(b) by 0 days.

This patent is subject to a terminal disclaimer.

(21) Appl. No.: 15/378,705

(22) Filed: Dec. 14, 2016

(65) Prior Publication Data

US 2017/0165184 A1  Jun. 15, 2017

(30) Foreign Application Priority Data

Dec. 15, 2015  (DE) ........................ 10 2015 225 212

(51) Int. Cl.
 *A61K 8/31* (2006.01)
 *A61K 8/81* (2006.01)
 *A61K 8/33* (2006.01)
 *A61K 8/34* (2006.01)
 *A61Q 5/06* (2006.01)

(52) U.S. Cl.
 CPC .............. *A61K 8/8158* (2013.01); *A61K 8/31* (2013.01); *A61K 8/315* (2013.01); *A61K 8/33* (2013.01); *A61K 8/34* (2013.01); *A61K 8/8152* (2013.01); *A61Q 5/06* (2013.01); *A61K 2800/594* (2013.01); *A61K 2800/87* (2013.01)

(58) Field of Classification Search
 CPC .......... A61K 2800/48; A61K 2800/594; A61K 2800/87; A61K 8/042; A61K 8/046; A61K 8/31; A61K 8/315; A61K 8/33; A61K 8/34; A61K 8/8152; A61K 8/8158; A61Q 5/06

See application file for complete search history.

(56) References Cited

U.S. PATENT DOCUMENTS

| | | | | |
|---|---|---|---|---|
| 4,874,604 A | * | 10/1989 | Sramek | A61K 8/046 424/47 |
| 5,176,898 A | * | 1/1993 | Goldberg | A61K 8/585 424/47 |
| 2008/0178899 A1 | * | 7/2008 | Moenks | A61K 8/046 132/203 |

FOREIGN PATENT DOCUMENTS

| | | |
|---|---|---|
| DE | 102004040172 A1 | 3/2006 |
| DE | 102014217207 A1 | 3/2016 |
| EP | 1726331 A1 | 5/2005 |
| EP | 1719499 A1 | 11/2006 |
| EP | 1719500 A1 | 11/2006 |
| WO | 2005012588 A1 | 2/2005 |
| WO | 2012054278 A2 | 4/2012 |

OTHER PUBLICATIONS

Preliminary Amendment for U.S. Appl. No. 15/360,250, dated Dec. 14, 2016.
Substitute Specification for U.S. Appl. No. 15/360,250 dated Dec. 14, 2016.
United Kingdom Intellectual Property Office, Combined Search and Examination Report under Section 17 & 18(3) issued in International Application No. GB1621144.3, dated Oct. 2, 2017.
Acydyne Hair Styling Plymers Product Overview, publicly available at http://msdssearch.dow.com/PublishedLiteratureDOWCOM/dh_0933/0901b80380933ea9.pdf. This web page was accessed for the attached document on Friday, Apr. 27, 2018.

* cited by examiner

*Primary Examiner* — Ernst V Arnold
(74) *Attorney, Agent, or Firm* — Lorenz & Kopf LLP

(57) ABSTRACT

Cosmetic agents and methods for the temporary deformation of keratin-containing fibers using the cosmetic agents are provided herein. In one embodiment, the cosmetic agent for the temporary shaping of keratinic fibers includes a cosmetic preparation. The cosmetic preparation includes at least one copolymer a1), made up of at least the following monomer units: (meth)acrylic acid, (meth)acrylic acid alkyl ester, and (meth)acrylic acid hydroxyalkyl ester. The cosmetic preparation further includes at least one copolymer a2), made up of at least the following monomer units: N-tert-butylacrylamide, acrylic acid, and ethyl acrylate. The weight proportion of copolymers a1) and a2) in terms of the total weight of the cosmetic preparation is about 10 to about 30% by weight.

20 Claims, No Drawings

AGENT AND METHOD FOR THE TEMPORARY SHAPING OF KERATIN-CONTAINING FIBERS

CROSS-REFERENCE TO RELATED APPLICATION

This application claims priority to German Patent Application No. 10 2015 225 212.4, filed Dec. 15, 2015, which is incorporated herein by reference in its entirety.

TECHNICAL FIELD

The present disclosure relates to a cosmetic composition for hair setting or for the temporary reshaping of keratinic fibers, in particular human hair, wherein the composition contains a combination of two specific copolymers in high concentration.

BACKGROUND

The temporary creation of hairstyles for a longer time period up to a number of days normally requires the use of active setting substances. Hair treatment agents used for a temporary shaping of the hair therefore play an important role. Suitable agents for temporary shaping typically contain synthetic polymers and/or waxes as an active setting substance. Agents for supporting the temporary reshaping of keratin-containing fibers can be produced, for example, as a hairspray, hair wax, hair gel, or hair foam.

The most important property of an agent for the temporary shaping of hair, also called a styling agent hereinafter, is to give the treated fibers the greatest possible hold in the new modelled shape, i.e., a shape imposed on the hair. This is also referred to as a strong hairstyle hold or a high degree of hold of the styling agent. The hairstyle hold is determined substantially by the type and amount of the employed active setting substances, but the other components of the styling agent may also have an effect.

In addition to a high degree of hold, styling agents must satisfy a wide range of further requirements. These can be divided roughly into properties on the hair, properties of the particular formulation, e.g., properties of the sprayed aerosol, and properties related to the handling of the styling agent, particular importance being attached to the properties on the hair. Mention can be made in particular of humidity resistance, low tackiness (tack), and a balanced conditioning effect. Furthermore, a styling agent should be universally usable, if possible, for all hair types and be gentle to the hair and skin.

In order to satisfy the different requirements, many synthetic polymers for use in styling agents were already developed as active setting substances. These polymers can be divided into cationic, anionic, nonionic, and amphoteric setting polymers.

The European patents EP 1719499 B1, EP 1719500 B1, and EP 1726331 B1 describe acrylate resins with the INCI name of Acrylates/Hydroxy Ester Acrylates Copolymer and their use in styling agents. The international patent application WO 2012/054278 A2 also mentions Acrylates/Hydroxy Ester Acrylates Copolymers as hair-setting polymers and used by way of an example Acudyne® 1000 (The Dow Chemical Company) in hair foams.

Hairsprays based on copolymers of N-tert-butylacrylamide, acrylic acid, and ethyl acrylate are described, among others, in the German patent application DE 10 2004 040 172 A1.

Not every polymer or not every polymer mixture is basically suitable for the production of hair styling agents. This applies in particular to hairsprays in which, for example, the viscosity and thereby also the spraying behavior are influenced by the polymer or the amount of the polymer employed.

Furthermore, not every polymer and every polymer mixture is suitable for producing highly concentrated hair styling agents. With an increasing polymer concentration, apart from the previously described problems with the viscosity and dispensability of the agents, furthermore, there are difficulties in regard to solubility and storage stability in particular of hairsprays.

A hairspray with a high polymer content (compact hairspray) is described, for example, in the international patent application WO 2005/012588 A2.

Even if suitable polymers and polymer combinations have been developed for some time for use in styling concentrates in the field of temporary hair shaping, the results achieved so far continue to leave room for improvement, particularly in regard to storage stability, applicability, and the degree of hold of these agents. Currently available styling agents in particular can still be improved with respect to the fact that a good combination of the degree of hold and long-term hold (high humidity curl retention) is not always sufficiently assured.

BRIEF SUMMARY

Cosmetic agents and methods for the temporary deformation of keratin-containing fibers using the cosmetic agents are provided herein. In one embodiment, the cosmetic agent for the temporary shaping of keratinic fibers includes a cosmetic preparation. The cosmetic preparation includes at least one copolymer a1), made up of at least the following monomer units: (meth)acrylic acid, (meth)acrylic acid alkyl ester, and (meth)acrylic acid hydroxyalkyl ester. The cosmetic preparation further includes at least one copolymer a2), made up of at least the following monomer units: N-tert-butylacrylamide, acrylic acid, and ethyl acrylate. The weight proportion of copolymers a1) and a2) in terms of the total weight of the cosmetic preparation is about 10 to about 30% by weight.

In another embodiment, a cosmetic product including a cosmetic agent and a dispensing device with a spray valve is provided. The cosmetic agent includes at least one copolymer a1), made up of at least the following monomer units: (meth)acrylic acid, (meth)acrylic acid alkyl ester, and (meth)acrylic acid hydroxyalkyl ester. The cosmetic agent further includes at least one copolymer a2), made up of at least the following monomer units: N-tert-butylacrylamide, acrylic acid, and ethyl acrylate. The weight proportion of copolymers a1) and a2) in terms of the total weight of the cosmetic agent is about 10 to about 30% by weight.

In another embodiment, the method for the temporary shaping of keratin-containing fibers includes the step of acting on the keratinic fibers by a cosmetic agent. The cosmetic agent includes at least one copolymer a1) composed at least of the following monomer units: (meth)acrylic acid, (meth)acrylic acid alkyl ester, and (meth)acrylic acid hydroxyalkyl ester. The cosmetic agent further includes at least one copolymer a2), made up of at least the following monomer units: N-tert-butylacrylamide, acrylic acid, and ethyl acrylate. The weight proportion of copolymers a1) and a2) in terms of the total weight of the cosmetic agent is about 10 to about 30% by weight. The method further includes the step of temporarily fixing the keratinic fibers into shape.

DETAILED DESCRIPTION

The following detailed description is merely exemplary in nature and is not intended to limit the disclosure or the application and uses of the disclosure. Furthermore, there is not intention to be bound by any theory presented in the preceding background or the following detailed description.

An object of the present disclosure was to provide other suitable polymer combinations, which are notable for good film-forming and/or setting properties and have a very high degree of hold without having to give up flexibility and good humidity resistance, in particular resistance to sweat and water. The polymer combinations should be suitable, moreover, for producing concentrated cosmetic compositions with a high chemical and physical stability and be easy to apply.

This was achieved as contemplated herein by a combination of two specific copolymers different from one another.

The present disclosure provides:

1. A cosmetic agent for the temporary shaping of keratinic fibers, comprising
   a) a cosmetic preparation containing
      a1) at least one copolymer, made up of at least the following monomer units:
         (meth)acrylic acid
         (meth)acrylic acid alkyl ester
         (meth)acrylic acid hydroxyalkyl ester;
      a2) at least one copolymer, made up of at least the following monomer units:
         N-tert-butylacrylamide
         acrylic acid
         ethyl acrylate,
   wherein the weight proportion of copolymers a1) and a2) in terms of the total weight of the cosmetic preparation is about 10 to about 30% by weight.

2. The cosmetic agent according to point 1, wherein the weight proportion of copolymers a1) and a2) in terms of the total weight of the cosmetic preparation is about 11 to about 25% by weight and in particular about 12 to about 20% by weight.

3. The cosmetic agent according to one of the preceding points, wherein the at least one copolymer a1), based on its total weight, consists of at least 90% by weight, preferably of at least 95% by weight, and in particular of at least 97% by weight of the monomers
   (meth)acrylic acid
   (meth)acrylic acid alkyl ester
   (meth)acrylic acid hydroxyalkyl ester.

4. The cosmetic agent according to one of the preceding points, wherein copolymer a1) has the INCI name Acrylates/Hydroxyesters Acrylates Copolymer.

5. The cosmetic agent according to one of the preceding points, wherein the preparation contains, based on its total weight, about 1.0 to about 15% by weight, preferably about 2.0 to about 14% by weight, and in particular about 4.0 to about 12% by weight of copolymer a1).

6. The cosmetic agent according to one of the preceding points, wherein the at least one copolymer a2), based on its total weight, consists of at least 90% by weight, preferably of at least 95% by weight, and in particular of at least 97% by weight of the monomers
   N-tert-butylacrylamide
   acrylic acid
   ethyl acrylate.

7. The cosmetic agent according to one of the preceding points, wherein copolymer a2) has the INCI name Acrylates/t-Butylacrylamide Copolymer.

8. The cosmetic agent according to one of the preceding points, wherein the preparation contains, based on its total weight, about 1.0 to about 15% by weight, preferably about 2.0 to about 14% by weight, and in particular about 4.0 to about 12% by weight of copolymer a2).

9. The cosmetic agent according to one of the preceding points, wherein the weight ratio of copolymer a1) to copolymer a2) is from about 1:7 to about 7:1, preferably from about 1:5 to about 5:1, and in particular from about 1:3 to about 3:1.

10. The cosmetic agent according to one of the preceding points, wherein the preparation contains, based on its total weight, about 30 to about 90% by weight, preferably about 40 to about 85% by weight, and in particular about 50 to about 80% by weight of ethanol.

11. The cosmetic agent according to one of the preceding points, wherein the preparation contains, based on its total weight, about 0.01 to about 30% by weight and in particular about 5.0 to about 25% by weight of water.

12. The cosmetic agent according to one of the preceding points, wherein the preparation consists, based on its total weight, of at least 70% by weight, preferably of at least 80% by weight, and in particular of at least 90% by weight of copolymers a1) and a2), ethanol, and water.

13. The cosmetic agent according to one of the preceding points, wherein preparation a) has a viscosity (Brookfield DV2T viscometer; 20° C., spindle 2, 10 rpm) of about 10 to about 1000 mPas, preferably of about 15 to about 500 mPas, and in particular of about 20 to about 200 mPas.

14. The cosmetic agent according to one of the preceding points, wherein the agent comprises, furthermore,
   b) at least one propellant.

15. The cosmetic agent according to one of the preceding points, wherein the agent comprises, furthermore,
   b) at least one propellant from the group comprising propane, a mixture of propane and butane, dimethyl ether, and 1,1-difluoroethane.

16. The cosmetic agent according to one of the preceding points, comprising, based on its total weight,
   a) about 30 to about 60% by weight of the cosmetic preparation,
   b) about 40 to about 70% by weight of propellant.

17. A cosmetic product comprising
   i. a cosmetic agent according to one of points 1 to 16,
   ii. a dispensing device with a spray valve.

18. The cosmetic product according to point 17, wherein the spray valve has a maximum valve opening of less than 0.4 mm, preferably between about 0.22 and about 0.32 mm, and in particular between about 0.25 and about 0.30 mm.

19. Use of an agent or a product according to one of points 1 to 18 for the temporary shaping of keratin-containing fibers, in particular human hair.

20. A method for the temporary shaping of keratin-containing fibers, in particular human hair, in which the keratinic fibers are acted upon by a cosmetic agent according to one of points 1 to 16 and are temporarily fixed in their shape.

21. The method according to point 20, wherein the application to the keratinic fibers occurs at a spray rate of the cosmetic preparation of about 18 to about 30 g/min, preferably of about 22 to about 28 g/min.

It was found surprisingly in the context of the present disclosure that an improved humidity resistance of styling products can be obtained by the combination of two components known per se, which are already used in styling products. Other usually required properties of styling products such as long-lasting hold, stiffness, and low tackiness are retained in this case. Even if the individual components are known, such a good combination of properties was itself not to be expected and was surprising. It was shown experimentally that by the combination of the two components a highly superadditive, therefore synergistic effect with respect to the humidity resistance and the degree of hold was obtained.

The term 'keratinic fibers' as contemplated herein covers pelts, wool, and feathers but in particular human hair.

The essential components of the cosmetic composition of the disclosure are anionic copolymer a1) and anionic copolymer a2) different from copolymer a1).

The cosmetic preparations of the disclosure contain an anionic copolymer a1) as a first essential component)

In regard to producibility, applicability, and cosmetic effect of the cosmetic agents of the disclosure, it has proven to be advantageous, if the weight proportion of copolymer a1) in terms of the total weight of cosmetic preparation a) is about 1.0 to about 15% by weight, preferably about 2.0 to about 14% by weight, and in particular of about 4.0 to about 12% by weight.

Copolymer a1) is derived from the monomers, (meth)acrylic acid, (meth)acrylic acid alkyl ester, and (meth)acrylic acid hydroxyalkyl ester, and optionally other monomers.

Preferred copolymers a1) consist preferably of at least 90% by weight, primarily at least 95% by weight, and in particular of at least 97% by weight of the monomers, (meth)acrylic acid, (meth)acrylic acid alkyl ester, and (meth)acrylic acid hydroxyalkyl ester. Particularly preferred copolymers a1) were obtained exclusively from the monomers, (meth)acrylic acid, (meth)acrylic acid alkyl ester, and (meth)acrylic hydroxyalkyl ester.

The cosmetic agents of a further preferred embodiment are characterized in that the at least one copolymer a1), based on its total weight, consists of at least 90% by weight, preferably of at least 95% by weight, and in particular of at least 97% by weight of the monomers
(meth)acrylic acid
(meth)acrylic acid alkyl ester
(meth)acrylic acid hydroxyalkyl ester.

The at least one methacrylic acid can be methacrylic acid or acrylic acid.

The alkyl group of the (meth)acrylic acid alkyl ester is preferably a C1-C8 alkyl group, which may be linear or branched. Examples of alkyl groups are methyl, ethyl, propyl, isopropyl, 1-butyl, 2-butyl, isobutyl, tert-butyl, linear or branched pentyl, linear or branched hexyl, linear or branched heptyl, and linear or branched octyl. More preferably, the alkyl group is a C1 to C5 alkyl group. According to an embodiment of the disclosure, two or more (meth)acrylic acid alkyl esters are contained, which differ with respect to the carbon number of the alkyl group. For example, a methacrylic acid C1-C3 alkyl ester and an acrylic acid C2-C5 alkyl ester are contained.

The hydroxyalkyl group of the (meth)acrylic acid hydroxyalkyl ester can be a hydroxy-C1-C10 alkyl group, preferably a hydroxy-C2-C5 alkyl group. In a preferred embodiment, the (meth)acrylic acid hydroxyalkyl ester unit is a (meth)acrylic acid hydroxyethyl ester.

The proportion of the units, (meth)acrylic acid, (meth)acrylic acid alkyl ester, and (meth)acrylic acid hydroxyalkyl ester, in acrylate resin a1) can vary over a broad range. The proportion of (meth)acrylic acid in the acrylate copolymer is preferably 2 to 50% by weight, more preferably 5 to 30% by weight. The proportion of the (meth)acrylic acid alkyl ester in the acrylate copolymer is preferably 5 to 95% by weight, more preferably 45 to 90% by weight. The proportion of (meth)acrylic acid hydroxyalkyl ester in the acrylate copolymer is preferably 2 to 70% by weight, more preferably 5 to 30% by weight.

The weight average of the molecular weight of the anionic acrylate copolymer a1) is preferably 130,000 to 160,000, more preferably 140,000 to 150,000, determined by gel permeation chromatography (GPC).

The viscosity of the anionic acrylate copolymer a1) used in the cosmetic composition at a solids content of about 44 to about 46% by weight and a pH of about 3.30 to about 4.30 at 25° C. is preferably at most 150 cPS (Brookfield LV, spindle 1, 60 rpm).

The previously described copolymers a1) are marketed, for example, under the name Acudyne® 1000 (INCI name: Acrylates/Hydroxyesters Acrylates Copolymer) by Rohm & Haas.

The cosmetic preparations of the disclosure contain an anionic copolymer a2) as a second essential component.

In regard to producibility, applicability, and cosmetic effect of cosmetic agents of the disclosure, it has proven advantageous, if the weight proportion of copolymer a2) in terms of the total weight of cosmetic preparation a) is about 1.0 to about 15% by weight, preferably about 2.0 to about 14% by weight, and in particular of about 4.0 to about 12% by weight.

Copolymer a2) is derived from the monomers, N-tert-butylacrylamide, acrylic acid, ethyl acrylate, and optionally other monomers.

Preferred copolymers a2) consist preferably of at least 90% by weight, primarily at least 95% by weight, and in particular of at least 97% by weight of the monomers, i) N-tert-butylacrylamide, ii) acrylic acid, and iii) ethyl acrylate. Particularly preferred copolymers a2) were obtained exclusively from the monomers: i) N-tert-butylacrylamide, ii) acrylic acid, and iii) ethyl acrylate.

Copolymers a2) described above are marketed, for example, under the name Ultrahold® 8 (INCI name: Acrylates/t-Butylacrylamide Copolymer; CAS number 26062-56-6) by BASF.

Copolymer a2) is used in the cosmetic agent preferably in a partially neutralized or neutralized form. Preferably at least one alkanolamine is used for neutralization. The alkanolamines that can be used as alkalizing agents of the disclosure are preferably selected from primary amines having a $C_2$-$C_6$ alkyl parent substance, which carries at least one hydroxyl group. Particularly preferred alkanolamines are selected from the group, formed by 2-aminoethan-1-ol (monoethanolamine), tris(2-hydroxyethyl)amine (triethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, and 2-amino-2-methylpropane-1,3-diol. Alkanolamines very particularly preferred as contemplated herein are selected from the group comprising 2-aminoethan-1-ol, 2-amino-2-methylpropan-1-ol, and 2-amino-2-methylpropane-1,3-diol. 2-Amino-2-methylpropanol has proven to be an especially suitable neutralizing agent. Cosmetic agents preferred as contemplated herein contain at least one alkanolamine, preferably 2-amino-2-methylpropanol. 2-Amino-2-methylpropanol is employed in the agents as contemplated herein preferably in an amount that does not exceed the amount necessary for the neutralization of copolymer a2). Preferably, the amounts, used in the agents of the disclosure, of 2-amino-2-methylpropanol are about 80 to 100%, particularly preferably about 90 to 100%, and in particular about 95 to 100% of the amount required for the complete neutralization of copolymer a2). In a preferred embodiment, the weight proportion of 2-amino-2-methylpropanol in terms of the total weight of cosmetic preparation a) is about 0.1 to about 4.0% by weight, preferably about 0.5 to about 3.0% by weight, and in particular about 1.0 to about 2.0% by weight.

The weight proportion of copolymers a1) and a2) in terms of the total weight of the cosmetic preparation is about 10 to about 30% by weight. Cosmetic preparations are preferred in which the weight proportion of copolymers a1) and a2) in terms of the total weight of the cosmetic preparation is about 11 to about 25% by weight and in particular about 12 to about 20% by weight.

Apart from the total weight proportion of copolymers a1) and a2), furthermore, the weight ratio of copolymers a1) and a2) to one another as well has an effect on the humidity resistance, degree of hold, and the other application properties of the cosmetic agents of the disclosure. Technically especially advantageous cosmetic agents are characterized in that the weight ratio of copolymer a1) to copolymer a2) is from about 1:7 to about 7:1, preferably from about 1:5 to about 5:1, and in particular from about 1:3 to about 3:1.

Apart from copolymers a1) and copolymers a2) described above, the cosmetic preparations of the disclosure can contain further active substances, auxiliary substances, and care substances.

A first group of active substances employed with preference are the film-forming polymers. These film-forming polymers in this case are not identical to the copolymer a1) or copolymer a2) described above. The weight proportion of the film-forming polymer in terms of the total weight of the cosmetic preparation is preferably about 0.1 to about 8.0% by weight, preferably about 0.5 to about 6.0% by weight, and in particular about 1.0 to about 4.0% by weight.

Nonionic polymers are used with particular preference as film-forming polymers. Suitable nonionic polymers are, for example:

vinylpyrrolidone/vinyl ester copolymers, as they are marketed, for example, under the trademark Luviskol® (BASF). Luviskol® VA 64 and Luviskol® VA 73, each being vinylpyrrolidone/vinyl acetate copolymers, are preferred nonionic polymers.

cellulose ethers, such as hydroxypropyl cellulose, hydroxyethyl cellulose, and methyl hydroxypropyl cellulose, as they are marketed, for example, under the trademarks Culminal® and Benecel® (AQUALON).

shellac.

polyvinylpyrrolidones, as they are marketed, for example, under the name Luviskol® (BASF).

siloxanes. These siloxanes can be both water-soluble and water-insoluble. Both volatile and nonvolatile siloxanes are suitable, nonvolatile siloxanes being understood to be compounds whose boiling point at normal pressure is above 200° C. Preferred siloxanes are polydialkylsiloxanes such as, for example, polydimethylsiloxane, polyalkylarylsiloxanes such as, for example, polyphenylmethylsiloxane, ethoxylated polydialkylsiloxanes, and polydialkylsiloxanes that contain amine and/or hydroxy groups.

glycosidically substituted silicones.

Because of their cosmetic effect in combination with copolymers a1) and a2), film-forming polymers preferably employed as contemplated herein are in particular the polyvinylpyrrolidones (INCI name: PVP) and the vinylpyrrolidone/vinyl acetate copolymers (INCI name: VP/VA Copolymer), the weight proportion of these polymers preferably being limited to amounts between about 1.0 and about 10% by weight. Particularly preferred cosmetic preparations of the disclosure are therefore characterized in that they contain, based on their total weight, further about 1.0 to about 10% by weight of polyvinylpyrrolidone and/or vinylpyrrolidone/vinyl acetate copolymer, preferably polyvinylpyrrolidone. Particularly preferred cosmetic preparations have a weight proportion of polyvinylpyrrolidone and/or vinylpyrrolidone/vinyl acetate copolymer c) in terms of the total weight of the cosmetic preparation of about 2.0 to about 8.5% by weight, preferably of about 3.0 to about 7.0% by weight.

In summary, cosmetic agents particularly preferred as contemplated herein with copolymers a1) and a2) and film-forming polymer a3) contain three polymers different from one another.

Protein hydrolysates and/or derivatives thereof can be used as care substances. Protein hydrolysates are product mixtures obtained by acid-, base-, or enzyme-catalyzed degradation of proteins. The term 'protein hydrolysates' as contemplated herein is also understood to mean total hydrolysates, as well as individual amino acids and derivatives thereof, and mixtures of different amino acids. The molar weight of protein hydrolysates usable as contemplated herein is between about 75 (the molar weight of glycine) and about 200,000; the molar weight is preferably about 75 to about 50,000 daltons, and very particularly preferably about 75 to about 20,000 daltons.

A further group of care substances are vitamins, provitamins, vitamin precursors, and/or derivatives thereof. In this case, the vitamins, provitamins, and vitamin precursors that are usually assigned to the groups A, B, C, E, F, and H are preferred as contemplated herein.

Other care substances are glycerol, propylene glycol, panthenol, caffeine, nicotinamide, and sorbitol.

Plant extracts, but also mono- or oligosaccharides and/or lipids can be used as care substances.

The composition of some of the employed cosmetic preparations a), in which the weight proportion of copolymers a1) and a2) in terms of the total weight of the cosmetic preparation is about 10 to about 30% by weight, preferably about 11 to about 25% by weight, and in particular about 12 to about 20% by weight, can be obtained from the following tables (quantities given in percent by weight based on the total weight of the cosmetic agent unless specified otherwise).

|  | Formula 1 | Formula 2 | Formula 3 | Formula 4 | Formula 5 |
| --- | --- | --- | --- | --- | --- |
| Copolymer a1)* | 1.0 to 15 | 1.5 to 14.5 | 2.0 to 14 | 3.0 to 13 | 4.0 to 12 |
| Copolymer a2)* | 1.0 to 15 | 1.5 to 14.5 | 2.0 to 14 | 3.0 to 13 | 4.0 to 12 |
| Optional additives | To 100 | To 100 | To 100 | To 100 | To 100 |

-continued

|  | Formula 6 | Formula 7 | Formula 8 | Formula 9 | Formula 10 |
|---|---|---|---|---|---|
| Acrylates/Hydroxyesters Acrylates Copolymer (INCI) | 1.0 to 15 | 1.5 to 14.5 | 2.0 to 14 | 3.0 to 13 | 4.0 to 12 |
| Copolymer a2)* | 1.0 to 15 | 1.5 to 14.5 | 2.0 to 14 | 3.0 to 13 | 4.0 to 12 |
| Optional additives | To 100 | To 100 | To 100 | To 100 | To 100 |

|  | Formula 11 | Formula 12 | Formula 13 | Formula 14 | Formula 15 |
|---|---|---|---|---|---|
| Copolymer a1)* | 1.0 to 15 | 1.5 to 14.5 | 2.0 to 14 | 3.0 to 13 | 4.0 to 12 |
| Acrylates/t-Butylacrylamide Copolymer (INCI) | 1.0 to 15 | 1.5 to 14.5 | 2.0 to 14 | 3.0 to 13 | 4.0 to 12 |
| Optional additives | To 100 | To 100 | To 100 | To 100 | To 100 |

|  | Formula 16 | Formula 17 | Formula 18 | Formula 19 | Formula 20 |
|---|---|---|---|---|---|
| Acrylates/Hydroxyesters Acrylates Copolymer (INCI) | 1.0 to 15 | 1.5 to 14.5 | 2.0 to 14 | 3.0 to 13 | 4.0 to 12 |
| Acrylates/t-Butylacrylamide Copolymer (INCI) | 1.0 to 15 | 1.5 to 14.5 | 2.0 to 14 | 3.0 to 13 | 4.0 to 12 |
| Optional additives | To 100 | To 100 | To 100 | To 100 | To 100 |

Preferred cosmetic agents are based on an aqueous, aqueous/alcoholic, or alcoholic carrier. Thus, preferred cosmetic agents, based on their total weight, contain about 40 to about 98% by weight, preferably about 60 to about 95% by weight, and in particular about 70 to about 92% by weight of a polar solvent, preferably a polar solvent from the group comprising water, ethanol, and isopropanol.

As already mentioned, in particular the lower alcohols, usually used for cosmetic purposes and having 1 to 4 carbon atoms, such as, for example, ethanol and isopropanol, can be contained as alcohols.

Apart from these alcoholic solvents, furthermore, water-soluble cosolvents can be used in particular in combination with water. Examples of particularly preferred cosolvents are glycerol and/or ethylene glycol and/or 1,2-propylene glycol, which are preferably used in an amount of 0 to 30% by weight based on cosmetic preparation a).

Together with the other above-described copolymers a1) and a2), the aqueous, aqueous/alcoholic, or alcoholic carriers preferably form an essential component of cosmetic preparations a) of the disclosure. Particularly preferred are cosmetic preparations that consist, based on their total weight, of at least 70% by weight, preferably of at least 80% by weight, and in particular of at least 90% by weight of copolymers a1) and a2), ethanol, and/or water.

The composition of some technically advantageous cosmetic preparations a) with a liquid carrier, in which the weight proportion of copolymers a1) and a2) in terms of the total weight of the cosmetic preparation is about 10 to about 30% by weight, preferably about 11 to about 25% by weight, and in particular about 12 to about 20% by weight, can be obtained from the following tables. (The quantities in percent by weight refer to the total weight of the cosmetic agent unless specified otherwise.)

|  | Formula 21 | Formula 22 | Formula 23 | Formula 24 | Formula 25 |
|---|---|---|---|---|---|
| Copolymer a1)* | 1.0 to 15 | 1.5 to 14.5 | 2.0 to 14 | 3.0 to 13 | 4.0 to 12 |
| Copolymer a2)* | 1.0 to 15 | 1.5 to 14.5 | 2.0 to 14 | 3.0 to 13 | 4.0 to 12 |
| Water and/or ethanol | 40 to 98 | 40 to 98 | 60 to 95 | 60 to 95 | 70 to 92 |
| Optional additives | To 100 | To 100 | To 100 | To 100 | To 100 |

|  | Formula 26 | Formula 27 | Formula 28 | Formula 29 | Formula 30 |
|---|---|---|---|---|---|
| Acrylates/Hydroxyesters Acrylates Copolymer (INCI) | 1.0 to 15 | 1.5 to 14.5 | 2.0 to 14 | 3.0 to 13 | 4.0 to 12 |
| Copolymer a2)* | 1.0 to 15 | 1.5 to 14.5 | 2.0 to 14 | 3.0 to 13 | 4.0 to 12 |
| Water and/or ethanol | 40 to 98 | 40 to 98 | 60 to 95 | 60 to 95 | 70 to 92 |
| Optional additives | To 100 | To 100 | To 100 | To 100 | To 100 |

|  | Formula 31 | Formula 32 | Formula 33 | Formula 34 | Formula 35 |
|---|---|---|---|---|---|
| Copolymer a1)* | 1.0 to 15 | 1.5 to 14.5 | 2.0 to 14 | 3.0 to 13 | 4.0 to 12 |
| Acrylates/t-Butylacrylamide Copolymer (INCI) | 1.0 to 15 | 1.5 to 14.5 | 2.0 to 14 | 3.0 to 13 | 4.0 to 12 |
| Water and/or ethanol | 40 to 98 | 40 to 98 | 60 to 95 | 60 to 95 | 70 to 92 |
| Optional additives | To 100 | To 100 | To 100 | To 100 | To 100 |

|  | Formula 36 | Formula 37 | Formula 38 | Formula 39 | Formula 40 |
|---|---|---|---|---|---|
| Acrylates/Hydroxyesters Acrylates Copolymer (INCI) | 1.0 to 15 | 1.5 to 14.5 | 2.0 to 14 | 3.0 to 13 | 4.0 to 12 |
| Acrylates/t-Butylacrylamide Copolymer (INCI) | 1.0 to 15 | 1.5 to 14.5 | 2.0 to 14 | 3.0 to 13 | 4.0 to 12 |
| Water and/or ethanol | 40 to 98 | 40 to 98 | 60 to 95 | 60 to 95 | 70 to 92 |
| Optional additives | To 100 | To 100 | To 100 | To 100 | To 100 |

*according to claim 1

Of course, it is not only the weight proportion of the liquid carrier in terms of the total weight of cosmetic preparation a) that can vary, but the weight ratio of the aqueous to alcoholic carrier is also changeable.

Preferred cosmetic preparations contain, based on their total weight, about 0.01 to about 30% by weight and in particular about 5.0 to about 25% by weight of water.

As already mentioned, in particular the lower alcohols, usually used for cosmetic purposes and having 1 to 4 carbon atoms, such as, for example, ethanol and isopropanol, can be contained as alcohols. Preferred cosmetic preparations contain, based on their total weight, about 30 to about 90, preferably about 40 to about 85% by weight, and in particular about 50 to about 80% by weight of ethanol.

The composition of some technically advantageous cosmetic preparations a) with a liquid carrier, in which the weight proportion of copolymers a1) and a2) in terms of the total weight of the cosmetic preparation is about 10 to about 30% by weight, preferably about 11 to about 25% by weight, and in particular about 12 to about 20% by weight, can be obtained from the following tables. (The quantities in percent by weight refer to the total weight of the cosmetic agent unless specified otherwise.)

ally and also in combination. Hydrophilic propellant gases such as, e.g., carbon dioxide, can also be used advantageously in the context of the present disclosure, if the proportion of hydrophilic gases is selected as low and a lipophilic propellant gas (e.g., propane/butane) is present in excess. Propane, n-butane, isobutane, and mixtures of said propellant gases are particularly preferred. Preferred cosmetic agents are characterized in that the agent comprises furthermore at least one propellant b) from the group comprising propane, a mixture of propane and butane, dimethyl ether, and 1,1-difluoroethane (INCI: Hydrofluorocarbon 152a).

Preferred cosmetic agents of the disclosure contain, based on their total weight, about 30 to about 60% by weight of cosmetic preparation a) and about 40 to about 70% by weight of propellant b).

The further composition of some preferred cosmetic agents, which comprise, in addition to cosmetic preparation a), further a propellant b), and in which the weight proportion of copolymers a1) and a2) in terms of the total weight of the cosmetic preparation is about 10 to about 30% by weight, preferably about 11 to about 25% by weight, and in particular about 12 to about 20% by weight, can be obtained from the following Table 1.

|  | Formula 41 | Formula 42 | Formula 43 | Formula 44 | Formula 45 |
|---|---|---|---|---|---|
| Copolymer a1)* | 1.0 to 15 | 1.5 to 14.5 | 2.0 to 14 | 3.0 to 13 | 4.0 to 12 |
| Copolymer a2)* | 1.0 to 15 | 1.5 to 14.5 | 2.0 to 14 | 3.0 to 13 | 4.0 to 12 |
| Ethanol | 30 to 90 | 30 to 90 | 40 to 85 | 40 to 85 | 50 to 80 |
| Water | 0.01 to 30 | 0.1 to 30 | 1.0 to 30 | 2.0 to 30 | 5.0 to 25 |
| Optional additives | To 100 | To 100 | To 100 | To 100 | To 100 |
|  | Formula 46 | Formula 47 | Formula 48 | Formula 49 | Formula 50 |
| Acrylates/Hydroxyesters Acrylates Copolymer (INCI) | 1.0 to 15 | 1.5 to 14.5 | 2.0 to 14 | 3.0 to 13 | 4.0 to 12 |
| Copolymer a2)* | 1.0 to 15 | 1.5 to 14.5 | 2.0 to 14 | 3.0 to 13 | 4.0 to 12 |
| Ethanol | 30 to 90 | 30 to 90 | 40 to 85 | 40 to 85 | 50 to 80 |
| Water | 0.01 to 30 | 0.1 to 30 | 1.0 to 30 | 2.0 to 30 | 5.0 to 25 |
| Optional additives | To 100 | To 100 | To 100 | To 100 | To 100 |
|  | Formula 51 | Formula 52 | Formula 53 | Formula 54 | Formula 55 |
| Copolymer a1)* | 1.0 to 15 | 1.5 to 14.5 | 2.0 to 14 | 3.0 to 13 | 4.0 to 12 |
| Acrylates/t-Butylacrylamide Copolymer (INCI) | 1.0 to 15 | 1.5 to 14.5 | 2.0 to 14 | 3.0 to 13 | 4.0 to 12 |
| Ethanol | 30 to 90 | 30 to 90 | 40 to 85 | 40 to 85 | 50 to 80 |
| Water | 0.01 to 30 | 0.1 to 30 | 1.0 to 30 | 2.0 to 30 | 5.0 to 25 |
| Optional additives | To 100 | To 100 | To 100 | To 100 | To 100 |
|  | Formula 56 | Formula 57 | Formula 58 | Formula 59 | Formula 60 |
| Acrylates/Hydroxyesters Acrylates Copolymer (INCI) | 1.0 to 15 | 1.5 to 14.5 | 2.0 to 14 | 3.0 to 13 | 4.0 to 12 |
| Acrylates/t-Butylacrylamide Copolymer (INCI) | 1.0 to 15 | 1.5 to 14.5 | 2.0 to 14 | 3.0 to 13 | 4.0 to 12 |
| Ethanol | 30 to 90 | 30 to 90 | 40 to 85 | 40 to 85 | 50 to 80 |
| Water | 0.01 to 30 | 0.1 to 30 | 1.0 to 30 | 2.0 to 30 | 5.0 to 25 |
| Optional additives | To 100 | To 100 | To 100 | To 100 | To 100 |

*according to claim 1

The cosmetic preparation is preferably sprayed onto the hair. Particularly preferably, this occurs with the use of a propellant (aerosol spray). Preferred cosmetic agents therefore comprise, in addition to cosmetic preparation a), further at least one propellant b).

Suitable propellants (propellant gases) are propane, propene, n-butane, isobutane, isobutene, n-pentane, pentene, isopentane, isopentene, methane, ethane, dimethyl ether, nitrogen, air, oxygen, laughing gas, 1,1,1,3-tetrafluoroethane, heptafluoro-n-propane, perfluoroethane, monochlorodifluoromethane, 1,1-difluoroethane, namely, both individu- In Table 1, the left column ("Formula x") in each case refers to one of the exemplary cosmetic preparations a) of Formulas 1 to 60 listed in the tables disclosed further above. The other columns two to five ("propellant") in each case indicate the amount of propellant combined with the particular cosmetic preparation. These quantities given in "% by weight" refer to the total weight of cosmetic preparation a) of the particular "Formula x" without propellant.

The quantity "50 to 200% by weight" in the following Table 1 corresponds to the addition of propellant to cosmetic preparation a) in an amount of about 50 to about 200% by weight of the weight of cosmetic preparation a). In other words, cosmetic preparation a) and propellant b) are present in this cosmetic agent in a weight ratio of about 100:50 to about 100:200 or of about 2:1 to about 1:2.

The cosmetic agents according to row 4, column 4 in the following Table 1 are accordingly a mixture of the propellant-free cosmetic preparation a) according to Formula 3 with a propane/butane mixture in a weight ratio of cosmetic preparation a) to propellant of about 100:50 to about 100:200. The entry in row 4, column 4 in other words describes a cosmetic agent for the temporary shaping of keratinic fibers, comprising a) a cosmetic preparation containing
  a1) about 2.0 to about 14% by weight of at least one copolymer, which is made up of at least the following monomer units:
    (meth)acrylic acid
    (meth)acrylic acid alkyl ester
    (meth)acrylic acid hydroxyalkyl ester;
  a2) about 2.0 to about 14% by weight of at least one copolymer, which is made up of at least the following monomer units:
    N-tert-butylacrylamide
    acrylic acid
    ethyl acrylate,
b) propellant from the group of propane/butane mixtures, wherein the weight proportion of copolymers a1) and a2) in terms of the total weight of the cosmetic preparation is about 10 to about 30% by weight and the weight ratio of cosmetic preparation a) to propellant b) is about 2:1 to about 1:2.

TABLE 1

| | Propellant [% by weight] | | | |
|---|---|---|---|---|
| Formula 1 | 50 to 200 | 50 to 200 DFE* | 50 to 200 P/B** | 50 to 200 DME*** |
| Formula 2 | 50 to 200 | 50 to 200 DFE* | 50 to 200 P/B** | 50 to 200 DME*** |
| Formula 3 | 50 to 200 | 50 to 200 DFE* | 50 to 200 P/B** | 50 to 200 DME*** |
| Formula 4 | 50 to 200 | 50 to 200 DFE* | 50 to 200 P/B** | 50 to 200 DME*** |
| Formula 5 | 50 to 200 | 50 to 200 DFE* | 50 to 200 P/B** | 50 to 200 DME*** |
| Formula 6 | 50 to 200 | 50 to 200 DFE* | 50 to 200 P/B** | 50 to 200 DME*** |
| Formula 7 | 50 to 200 | 50 to 200 DFE* | 50 to 200 P/B** | 50 to 200 DME*** |
| Formula 8 | 50 to 200 | 50 to 200 DFE* | 50 to 200 P/B** | 50 to 200 DME*** |
| Formula 9 | 50 to 200 | 50 to 200 DFE* | 50 to 200 P/B** | 50 to 200 DME*** |
| Formula 10 | 50 to 200 | 50 to 200 DFE* | 50 to 200 P/B** | 50 to 200 DME*** |
| Formula 11 | 50 to 200 | 50 to 200 DFE* | 50 to 200 P/B** | 50 to 200 DME*** |
| Formula 12 | 50 to 200 | 50 to 200 DFE* | 50 to 200 P/B** | 50 to 200 DME*** |
| Formula 13 | 50 to 200 | 50 to 200 DFE* | 50 to 200 P/B** | 50 to 200 DME*** |
| Formula 14 | 50 to 200 | 50 to 200 DFE* | 50 to 200 P/B** | 50 to 200 DME*** |
| Formula 15 | 50 to 200 | 50 to 200 DFE* | 50 to 200 P/B** | 50 to 200 DME*** |
| Formula 16 | 50 to 200 | 50 to 200 DFE* | 50 to 200 P/B** | 50 to 200 DME*** |
| Formula 17 | 50 to 200 | 50 to 200 DFE* | 50 to 200 P/B** | 50 to 200 DME*** |
| Formula 18 | 50 to 200 | 50 to 200 DFE* | 50 to 200 P/B** | 50 to 200 DME*** |
| Formula 19 | 50 to 200 | 50 to 200 DFE* | 50 to 200 P/B** | 50 to 200 DME*** |
| Formula 20 | 50 to 200 | 50 to 200 DFE* | 50 to 200 P/B** | 50 to 200 DME*** |
| Formula 21 | 50 to 200 | 50 to 200 DFE* | 50 to 200 P/B** | 50 to 200 DME*** |
| Formula 22 | 50 to 200 | 50 to 200 DFE* | 50 to 200 P/B** | 50 to 200 DME*** |
| Formula 23 | 50 to 200 | 50 to 200 DFE* | 50 to 200 P/B** | 50 to 200 DME*** |
| Formula 24 | 50 to 200 | 50 to 200 DFE* | 50 to 200 P/B** | 50 to 200 DME*** |
| Formula 25 | 50 to 200 | 50 to 200 DFE* | 50 to 200 P/B** | 50 to 200 DME*** |
| Formula 26 | 50 to 200 | 50 to 200 DFE* | 50 to 200 P/B** | 50 to 200 DME*** |
| Formula 27 | 50 to 200 | 50 to 200 DFE* | 50 to 200 P/B** | 50 to 200 DME*** |
| Formula 28 | 50 to 200 | 50 to 200 DFE* | 50 to 200 P/B** | 50 to 200 DME*** |
| Formula 29 | 50 to 200 | 50 to 200 DFE* | 50 to 200 P/B** | 50 to 200 DME*** |
| Formula 30 | 50 to 200 | 50 to 200 DFE* | 50 to 200 P/B** | 50 to 200 DME*** |
| Formula 31 | 50 to 200 | 50 to 200 DFE* | 50 to 200 P/B** | 50 to 200 DME*** |
| Formula 32 | 50 to 200 | 50 to 200 DFE* | 50 to 200 P/B** | 50 to 200 DME*** |
| Formula 33 | 50 to 200 | 50 to 200 DFE* | 50 to 200 P/B** | 50 to 200 DME*** |
| Formula 34 | 50 to 200 | 50 to 200 DFE* | 50 to 200 P/B** | 50 to 200 DME*** |
| Formula 35 | 50 to 200 | 50 to 200 DFE* | 50 to 200 P/B** | 50 to 200 DME*** |
| Formula 36 | 50 to 200 | 50 to 200 DFE* | 50 to 200 P/B** | 50 to 200 DME*** |
| Formula 37 | 50 to 200 | 50 to 200 DFE* | 50 to 200 P/B** | 50 to 200 DME*** |
| Formula 38 | 50 to 200 | 50 to 200 DFE* | 50 to 200 P/B** | 50 to 200 DME*** |
| Formula 39 | 50 to 200 | 50 to 200 DFE* | 50 to 200 P/B** | 50 to 200 DME*** |
| Formula 40 | 50 to 200 | 50 to 200 DFE* | 50 to 200 P/B** | 50 to 200 DME*** |
| Formula 41 | 50 to 200 | 50 to 200 DFE* | 50 to 200 P/B** | 50 to 200 DME*** |
| Formula 42 | 50 to 200 | 50 to 200 DFE* | 50 to 200 P/B** | 50 to 200 DME*** |
| Formula 43 | 50 to 200 | 50 to 200 DFE* | 50 to 200 P/B** | 50 to 200 DME*** |
| Formula 44 | 50 to 200 | 50 to 200 DFE* | 50 to 200 P/B** | 50 to 200 DME*** |
| Formula 45 | 50 to 200 | 50 to 200 DFE* | 50 to 200 P/B** | 50 to 200 DME*** |
| Formula 46 | 50 to 200 | 50 to 200 DFE* | 50 to 200 P/B** | 50 to 200 DME*** |
| Formula 47 | 50 to 200 | 50 to 200 DFE* | 50 to 200 P/B** | 50 to 200 DME*** |
| Formula 48 | 50 to 200 | 50 to 200 DFE* | 50 to 200 P/B** | 50 to 200 DME*** |
| Formula 49 | 50 to 200 | 50 to 200 DFE* | 50 to 200 P/B** | 50 to 200 DME*** |
| Formula 50 | 50 to 200 | 50 to 200 DFE* | 50 to 200 P/B** | 50 to 200 DME*** |
| Formula 51 | 50 to 200 | 50 to 200 DFE* | 50 to 200 P/B** | 50 to 200 DME*** |
| Formula 52 | 50 to 200 | 50 to 200 DFE* | 50 to 200 P/B** | 50 to 200 DME*** |
| Formula 53 | 50 to 200 | 50 to 200 DFE* | 50 to 200 P/B** | 50 to 200 DME*** |
| Formula 54 | 50 to 200 | 50 to 200 DFE* | 50 to 200 P/B** | 50 to 200 DME*** |
| Formula 55 | 50 to 200 | 50 to 200 DFE* | 50 to 200 P/B** | 50 to 200 DME*** |
| Formula 56 | 50 to 200 | 50 to 200 DFE* | 50 to 200 P/B** | 50 to 200 DME*** |
| Formula 57 | 50 to 200 | 50 to 200 DFE* | 50 to 200 P/B** | 50 to 200 DME*** |
| Formula 58 | 50 to 200 | 50 to 200 DFE* | 50 to 200 P/B** | 50 to 200 DME*** |

TABLE 1-continued

| | Propellant [% by weight] | | | |
|---|---|---|---|---|
| Formula 59 | 50 to 200 | 50 to 200 DFE* | 50 to 200 P/B** | 50 to 200 DME*** |
| Formula 60 | 50 to 200 | 50 to 200 DFE* | 50 to 200 P/B** | 50 to 200 DME*** |

*"DFE" corresponds 1,1-difluorethane
**"P/B" corresponds a propane/butane mixture
***"DME" corresponds to dimethyl ether Vessels made of metal (aluminum, tin plate, tin), protected or non-splintering plastic or of glass that is externally coated with plastic may be used as compressed gas containers for aerosol applications; pressure resistance and breaking strength, corrosion resistance, ease of filling, as well as aesthetic aspects, handling, printability, etc., play a role in their selection. Special protective interior coatings assure corrosion resistance to cosmetic agent a).

If the agents of the disclosure are to be sprayed onto the hair, these agents are advantageously provided with a dispensing device and a spray valve. The resulting cosmetic products comprise accordingly a cosmetic agent of the disclosure and a dispensing device with a spray valve. Spray valves are preferred that have a maximum valve opening less than 0.4 mm, preferably between about 0.22 and about 0.32 mm, and in particular between about 0.25 and about 0.30 mm. The valve opening area is preferably about $60 \times 10^{-3}$ to about $100 \times 10^{-3}$ mm$^2$.

The spray rate in the method of the disclosure is preferably from about 18 to about 30 g/min, in particular from about 22 to about 28 g/min.

The spray rate is determined, apart from by the pressure within of the compressed gas container and the valve opening, furthermore also by the viscosity of cosmetic preparation a). Preferred cosmetic agents are characterized in that preparation a) has a viscosity (Brookfield DV2T viscometer; 20° C., spindle 2, 10 rpm) of about 10 to about 1000 mPas, preferably of about 15 to about 500 mPas, and in particular of about 20 to about 200 mPas.

In a preferred embodiment of the disclosure, the valve has a valve cone covered with a coating or a polymeric plastic A, and a flexible element of this kind with a reset function, which after the operation ends resets the valve to the closed position (=neutral position of the valve). Corresponding cosmetic products in which the aerosol dispensing device comprises a valve, which has a valve cone and/or a flexible element with a reset function and is/are covered with a coating or a polymeric plastic A, are preferred as contemplated herein.

In another preferred embodiment of the disclosure, the valve has a flexible element with a reset function and/or a valve cone made of at least one plastic B, preferably an elastomeric plastic. Here as well, cosmetic products of the disclosure in which the valve has a flexible element with a reset function and/or a valve cone made of at least one plastic B, are preferred, preferred plastics B being elastomeric plastics. Particularly preferred elastomeric plastics are selected from Buna, particularly Buna N, Buna 421, Buna 1602, and Buna KA 6712, neoprene, butyl, and chlorobutyl.

In another preferred embodiment of the disclosure, the flexible element with a reset function can be formed as a spiral spring or helical compression spring. In another preferred embodiment of the disclosure, the flexible element with the reset function can be formed integrally with the valve cone and have flexible legs.

As initially stated, the previously described cosmetic agents are characterized by particular hair-cosmetic properties, in particular advantageous properties during temporary hair shaping. A second subject of the present application therefore is the use of an agent of the disclosure for the temporary shaping of keratin-containing fibers, in particular human hair.

A third subject of the present application is a method for the temporary shaping of keratin-containing fibers, in particular human hair, in which the keratinic fibers are acted upon by a cosmetic agent of the disclosure and are fixed temporarily in their shape.

While at least one exemplary embodiment has been presented in the foregoing detailed description of the disclosure, it should be appreciated that a vast number of variations exist. It should also be appreciated that the exemplary embodiment or exemplary embodiments are only examples, and are not intended to limit the scope, applicability, or configuration of the disclosure in any way. Rather, the foregoing detailed description will provide those skilled in the art with a convenient road map for implementing an exemplary embodiment of the disclosure. It being understood that various changes may be made in the function and arrangement of elements described in an exemplary embodiment without departing from the scope of the disclosure as set forth in the appended claims.

The invention claimed is:

1. A cosmetic agent for the temporary shaping of keratinic fibers, comprising:
   a cosmetic preparation comprising:
      at least one copolymer a1), made up of at least the following monomer units;
         (meth)acrylic acid,
         (meth)acrylic acid alkyl ester, and
         (meth)acrylic acid hydroxyalkyl ester;
      at least one copolymer a2), made up of at least the following monomer units;
         N-tert-butylacrylamide,
         acrylic acid, and
         ethyl acrylate; and
      a film-forming polymer that is not identical to copolymer a1) or copolymer a2), wherein the film-forming polymer comprises a glycosidically substituted silicone;
   wherein the weight proportion of copolymers a1) and a2) in terms of the total weight of the cosmetic preparation is about 10 to about 30% by weight, and wherein the amount by weight of the film-forming polymer in the total weight of the cosmetic preparation is from about 0.5% to about 6.0% by weight.

2. The cosmetic agent according to claim 1, wherein the weight proportion of copolymers a1) and a2) in terms of the total weight of the cosmetic preparation is about 11 to about 25% by weight.

3. The cosmetic agent according to claim 1, wherein the preparation comprises, based on its total weight, about 1.0 to about 15% by weight of copolymer a1).

4. The cosmetic agent according to claim 1, wherein the preparation comprises, based on its total weight, about 1.0 to about 15% by weight of copolymer a2).

5. The cosmetic agent according to claim 1, wherein the preparation comprises, based on its total weight, about 30 to about 90% by weight of ethanol.

6. The cosmetic agent according to claim 1, wherein the preparation comprises, based on its total weight, about 0.01 to about 30% by weight of water.

7. The cosmetic agent according to claim 1, wherein the agent comprises, furthermore, at least one propellant.

8. The cosmetic agent according to claim 1, wherein the weight proportion of copolymers a1) and a2) in terms of the total weight of the cosmetic preparation is about 12 to about 20% by weight.

9. The cosmetic agent according to claim 1, wherein the preparation comprises, based on its total weight, about 2.0 to about 14% by weight of copolymer a1).

10. The cosmetic agent according to claim 1, wherein the preparation comprises, based on its total weight, about 4.0 to about 12% by weight of copolymer a1).

11. The cosmetic agent according to claim 1, wherein the preparation-comprises, based on its total weight, about 2.0 to about 14% by weight of copolymer a2).

12. The cosmetic agent according to claim 1, wherein the preparation-comprises, based on its total weight, about 4.0 to about 12% by weight of copolymer a2).

13. The cosmetic agent according to claim 1, wherein the preparation-comprises, based on its total weight, about 40 to about 85% by weight of ethanol.

14. The cosmetic agent according to claim 1, wherein the preparation comprises, based on its total weight, about 50 to about 85% by weight of ethanol.

15. The cosmetic agent according to claim 1, wherein the preparation-comprises, based on its total weight, about 5.0 to about 25% by weight of water.

16. The cosmetic agent according to claim 1, wherein copolymer a1) has the INCI name Acrylates/Hydroxyesters Acrylates Copolymer.

17. The cosmetic agent according to claim 1, wherein copolymer a2) has the INCI name Acrylates/t-Butylacrylamide Copolymer.

18. A cosmetic product, comprising:
 a cosmetic agent comprising:
  at least one copolymer a1), made up of at least the following monomer units;
   (meth)acrylic acid,
   (meth)acrylic acid alkyl ester, and
   (meth)acrylic acid hydroxyalkyl ester;
  at least one copolymer a2), made up of at least the following monomer units;
   N-tert-butylacrylamide,
   acrylic acid, and
   ethyl acrylate; and
  a film-forming polymer that is not identical to copolymer a1) or copolymer a2), wherein the film-forming polymer comprises a glycosidically substituted silicone;
  wherein the weight proportion of copolymers a1) and a2) in terms of the total weight of the cosmetic agent is about 10 to about 30% by weight, and wherein the amount by weight of the film-forming polymer in the total weight of the cosmetic preparation is from about 0.5% to about 6.0% by weight; and
 a dispensing device with a spray valve.

19. The cosmetic product according to claim 18, wherein the cosmetic agent further comprises at least one of ethanol or water.

20. A method for the temporary shaping of keratin-containing fibers, the method comprising the steps of:
 acting on the keratinic fibers by a cosmetic agent comprising:
  at least one copolymer a1), made up of at least the following monomer units;
   (meth)acrylic acid,
   (meth)acrylic acid alkyl ester, and
   (meth)acrylic acid hydroxyalkyl ester;
  at least one copolymer a2), made up of at least the following monomer units;
   N-tert-butylacrylamide,
   acrylic acid, and
   ethyl acrylate; and
  a film-forming polymer that is not identical to copolymer a1) or copolymer a2), wherein the film-forming polymer comprises a glycosidically substituted silicone;
  wherein the weight proportion of copolymers a1) and a2) in terms of the total weight of the cosmetic agent is about 10 to about 30% by weight, and wherein the amount by weight of the film-forming polymer in the total weight of the cosmetic preparation is from about 0.5% to about 6.0% by weight; and
 temporarily fixing the keratinic fibers into shape.

\* \* \* \* \*